United States Patent
Brida et al.

(10) Patent No.: US 6,200,458 B1
(45) Date of Patent: Mar. 13, 2001

(54) METHOD AND ARRANGEMENT FOR DETECTING THE OXYGEN CONTENT IN A GAS

(75) Inventors: Peter Brida, Vaihingen/Enz; Theodor Graser; Gerhard Hoetzel, both of Stuttgart, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/223,970

(22) Filed: Dec. 31, 1998

(30) Foreign Application Priority Data

Jan. 2, 1998 (DE) .............................. 198 00 027

(51) Int. Cl.[7] ......................... G01N 27/409; G01N 27/41
(52) U.S. Cl. ..................... 205/784; 205/784.5; 204/406; 204/424; 204/425
(58) Field of Search .................................... 204/424, 425, 204/427, 426, 402, 400, 421, 406; 205/784.5, 775, 784

(56) References Cited

U.S. PATENT DOCUMENTS

| | | | |
|---|---|---|---|
| 4,384,935 | * | 5/1983 | De Jong ............................. 204/406 |
| 4,902,401 | * | 2/1990 | Lin et al. .............................. 204/427 |
| 4,988,418 | * | 1/1991 | Beck et al. ......................... 204/153.1 |
| 5,080,775 | * | 1/1992 | Yamauchi et al. .................... 204/424 |
| 5,389,225 | * | 2/1995 | Aagard et al. ........................ 204/426 |
| 5,611,909 | * | 3/1997 | Studer ................................. 205/775 |
| 5,632,883 | | 5/1997 | Hoetzel . |
| 5,974,857 | * | 11/1999 | Yamashita et al. ................. 73/23.32 |

FOREIGN PATENT DOCUMENTS 52-071293 * 6/1977 (JP) .

\* cited by examiner

Primary Examiner—Robert J. Warden, Sr.
Assistant Examiner—Kaj K. Olsen
(74) Attorney, Agent, or Firm—Walter Ottesen

(57) ABSTRACT

The invention is directed to a method for detecting the oxygen content in a gas to be measured. At least one concentration cell operating in accordance with the Nernst principle is provided. The concentration cell includes a measuring electrode communicating with the gas and a solid electrolyte and a reference electrode connected to the measuring electrode through the solid electrolyte. A pump-current pulse is applied between the reference electrode and the measuring electrode and, directly after the end of each pump-current pulse, the current flow between the reference electrode and the measuring electrode is reversed in a pulse-like manner.

12 Claims, 2 Drawing Sheets

METHOD AND ARRANGEMENT FOR DETECTING THE OXYGEN CONTENT IN A GAS

FIELD OF THE INVENTION

The invention relates to a method for detecting the oxygen content of a gas by means of at least one concentration cell having a measuring electrode. The concentration cell operates in accordance with the Nernst principle and the measuring electrode communicates with the gas to be measured. The concentration cell also includes a reference electrode connected to the measurement electrode via a solid electrolyte. Periodic pump current pulses are preferably applied across the measurement and reference electrodes. The invention also relates to an arrangement for detecting the oxygen content in a gas.

BACKGROUND OF THE INVENTION

A method of the kind described above is disclosed, for example, in U.S. Pat. No. 5,632,883. The application of periodic pump current pulses to the measurement and reference electrodes affords the advantage that, in this way, two switching states occur. In the first state, the current source is coupled to the concentration cell and, in the second state, the current source is decoupled from the concentration cell so that the voltage, which serves as the measurement signal, between the measurement and reference electrode is not influenced by the current source in the decoupled state. In this way, a disturbance of the measurement signal because of the in-coupling of the current is eliminated. This in-coupling of the current leads to an additive voltage component of the measurement signal which, in turn, defines a disturbance of the measurement signal because of the temperature dependency of the internal resistance of the solid electrolyte.

In such a method and arrangement for detecting the oxygen content in a gas, it is problematic that, for a clocked pump reference, the reference pump current must be selected higher than for a non-clocked pump reference in order to obtain, over a time average, an adequate oxygen partial pressure in the concentration cell.

This leads to the situation that intense polarization effects occur on the concentration cell because of the higher pump current especially in the cold state of the concentration cell. Therefore, the actual sensor signal is made incorrect because of the polarization effects. Additive voltage components on the actual measurement signal occur because of the polarization effects. These voltage components lead to a signal shift which is present even after the pump current pulses.

SUMMARY OF THE INVENTION

In view of the foregoing, it is an object of the invention to provide a method for detecting the oxygen content in a gas which is so improved that errors of the measurement signal are minimized or completely eliminated. These errors are caused by polarization effects in the measurement probe.

The method of the invention is for detecting the oxygen content in a gas to be measured. The method includes the steps of: providing at least one concentration cell operating in accordance with the Nernst principle with the concentration cell including: a measuring electrode communicating with the gas; a solid electrolyte; and, a reference electrode connected to the measuring electrode through the solid electrolyte; applying a pump-current pulse between the reference electrode and the measuring electrode; and, directly after the end of each pump-current pulse, reversing the current flow between the reference electrode and the measuring electrode in a pulse-like manner.

A very rapid decay of the polarizations in the concentration cell is made possible by this pulse-like reversal of the current which flows between the reference electrode and the measurement electrode In principle, the most different possibilities exist for reversing the current flow between the reference electrode and the measurement electrode.

An advantageous embodiment provides that a current pulse of a pregiven duration and of a pregiven current intensity is applied between the reference electrode and the measurement electrode. The current pulse flows in the reverse direction. With this counter-current pulse, a shift of the probe voltage is most significantly reduced. This shift is caused by the polarization effects.

Advantageously, the duration and the current strength of the counter-current pulses are so selected that the charge, which is generated by the counter-current pulses, is significantly less than the charge generated by the pump current pulses.

Another embodiment provides that a short circuit of a short duration (short-circuit pulse) is effected between the reference electrode and the measurement electrode. This embodiment is especially simple to realize. Shifts of the probe voltage are almost entirely reduced even with such a short-circuit pulse. These shifts are caused by the polarization effects in the concentration cell.

The invention also relates to an arrangement for detecting the oxygen content in a gas. The arrangement includes at least a concentration cell, which operates in accordance with the Nernst principle. The concentration cell has a measurement electrode communicating with the gas to be measured and a reference electrode which is connected to the measurement electrode via a solid electrolyte and is in contact with a reference gas volume. The concentration cell also includes a pump current source via which preferably periodic pump current pulses can be coupled between the reference and measurement electrodes.

With reference to the above, it is a further object of the invention to improve an arrangement of the kind described above for detecting the oxygen content in a gas so that a very rapid reduction of the changes of the measurement voltage can be realized. These changes are caused by the polarization effects in the concentration cell.

According to another feature of the invention, a switch device is provided with which, after each pump current pulse, a short circuit or a low-ohmage connection is provided over a pregiven time span (short-circuit pulse) between the measurement electrode and the reference electrode.

Up to now, no detailed description has been provided as to the form of the counter-current pulse and of the short-circuit pulse. Advantageously, the counter-current pulse or the short-circuit pulse are shorter than the pump current pulse. In this way, it is avoided that there is a pumping off of the oxygen from the reference chamber of the concentration cell after a reduction of the polarization effects.

Preferably, the duration of the counter-current pulse or of the short-circuit pulse is approximately one twentieth to one tenth of the duration of the pump current pulse.

Furthermore, the duration and the current intensity of the counter-current pulses is so pregiven that the charge, which is generated by the counter-current pulses, is significantly less than the charge generated by the pump current pulses.

BRIEF DESCRIPTION OF THE DRAWINGS

The invention will now be explained with reference to the drawings wherein.

DESCRIPTION OF THE PREFERRED EMBODIMENTS OF THE INVENTION

Figure 1:
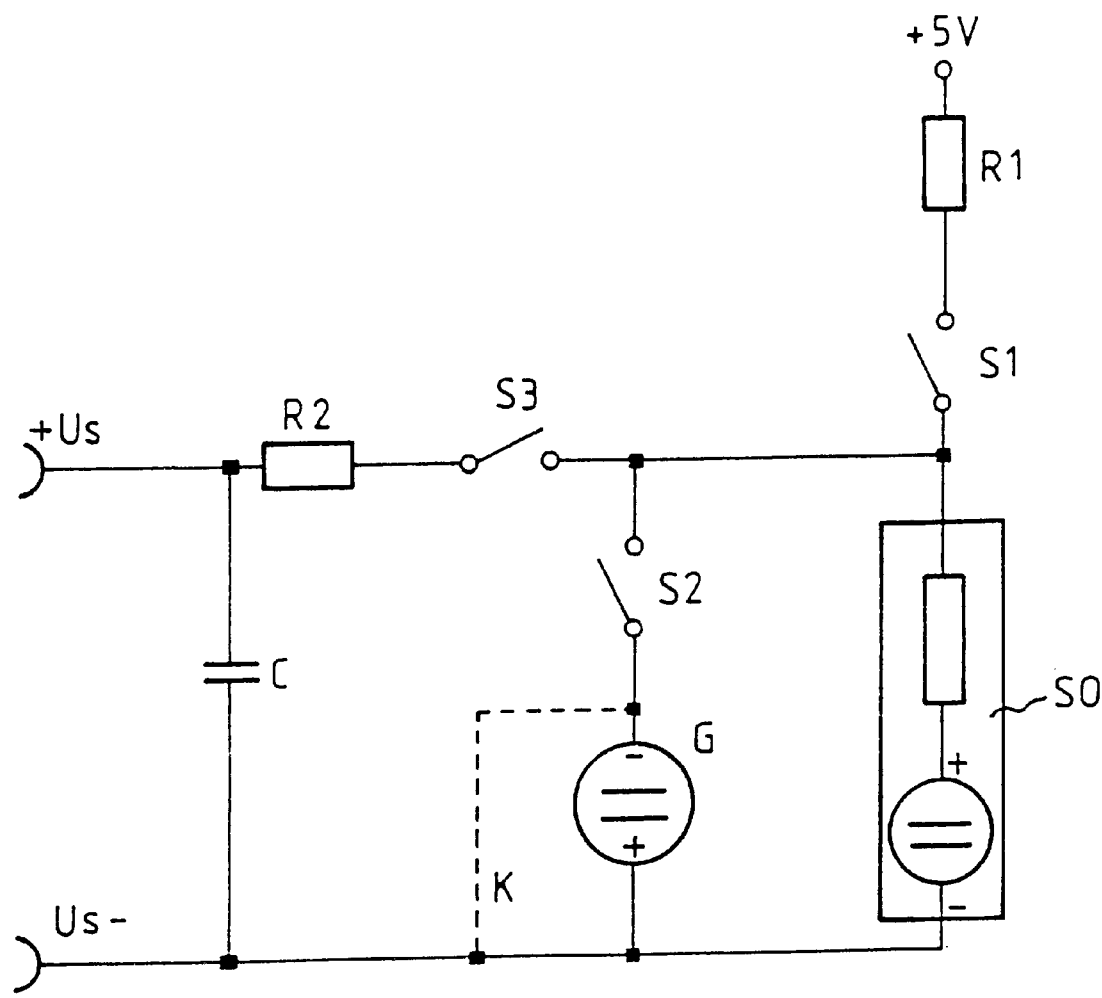
FIG. 1 is a schematic of an embodiment of an arrangement of the invention for detecting the oxygen content in a gas utilizing a concentration cell; and, FIG. 2 is a schematic of the control sequences of the switches shown in FIG. 1 as well as of the probe voltage resulting therefrom.

One embodiment of an arrangement for detecting the oxygen content in a gas is shown in FIG. 1 and includes a probe SO known per se, such as a lambda probe. The probe includes a measuring electrode which communicates with the gas to be measured and a reference electrode which communicates with a reference gas volume. The reference electrode is connected via a solid electrolyte to the measuring gas electrode. The reference gas volume is so separated from the gas to be measured that a particle exchange between the reference gas volume and the gas to be measured is made more difficult. The probe voltage US, which can be tapped via the probe, is an index for the oxygen content of the gas to be measured. A probe of this kind is disclosed in detail, for example, in U.S. Pat. No. 5,632,883, incorporated herein by reference.

As shown in FIG. 1, the probe voltage US can be tapped via a switch device such as a switch S3. An RC filter is connected downstream of :he switch S3 as shown. In the embodiment shown, the RC filter is a lowpass filter and comprises a resistor R2 and a capacitor C. The switch S3 is closed during the measuring phases so that the probe voltage US, which drops across the probe SO, can be tapped. In addition, a further switch device such as a switch S1 is provided to ensure that an adequately high oxygen partial pressure is present in the reference gas volume. A pump reference current can be supplied to the probe via the switch S1.

As shown in FIG. 1, a current flows via the resistor R1 when the switch S1 is in the closed state. This current flows into the measuring probe SO. The current is supplied periodically and in the form of pulses as will be described further below.

In addition, a counter-current source G is provided which can be connected in parallel to the probe via a switch device such as a switch S2. As an alternative to the counter-current source G, a short-circuit line K can be provided which likewise can be connected via the switch S2 in parallel to probe SO. The switch S2 is actuated directly after the opening of switch S1. In this way, it is ensured that a counter-current pulse or a short-circuit pulse is applied across the measuring electrode and the probe electrode directly after a pump current pulse was supplied to the probe SO. A reduction of the polarization effects is obtained via this counter-current pulse or short-circuit pulse. The polarization effects build up because of the pump current pulse.

A method for detecting the oxygen content in the gas to be measured is described in the following with reference to FIG. 1 and especially with reference to FIG. 2.

Figure 2:
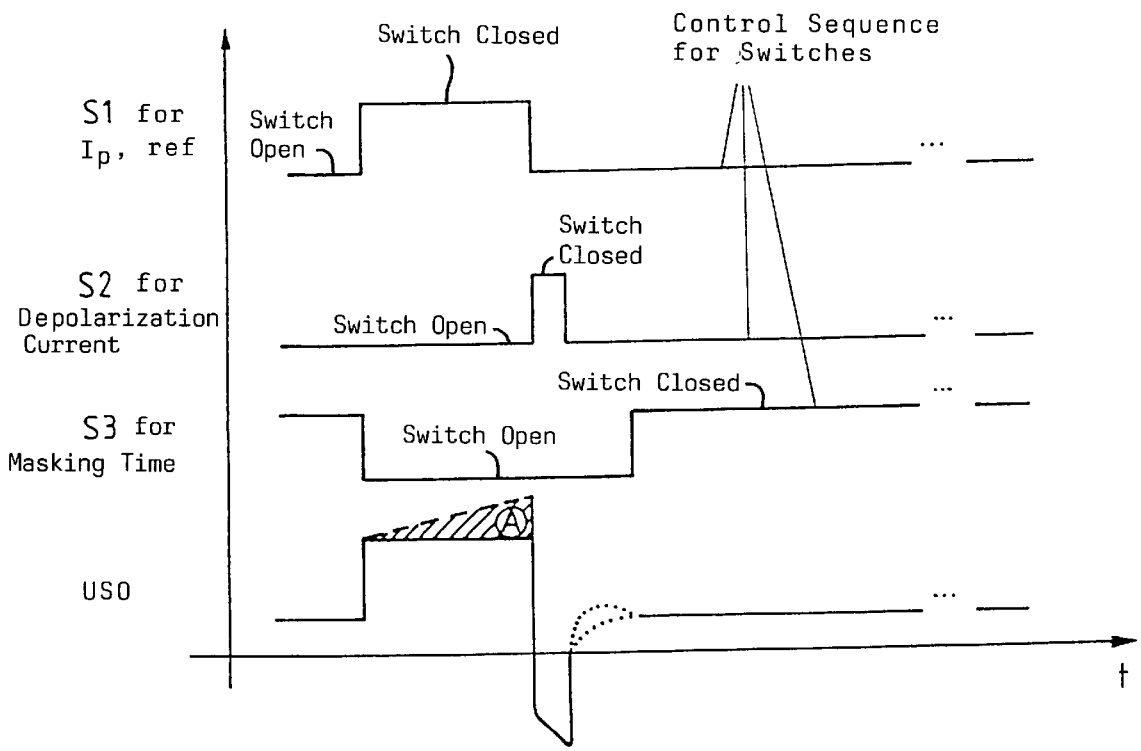

In FIG. 2, the control sequences of the switches (S1, S2, S3), which are shown in FIG. 1, as well as the probe voltage USO are shown schematically as a function of time (t). The probe voltage USO can be tapped via the probe SO.

For the sake of clarity, the switching state is shown for only a pump current pulse, a counter-current pulse as well as the probe voltage signal trace resulting therefrom. It is understood that these switching states and the probe voltage signal trace repeat periodically.

As shown in FIG. 2, directly after a pump current pulse is applied to the probe SO, a counter-current pulse or short-circuit pulse is applied. The pump current pulse is applied by closing the switch S1 and the counter-current pulse is applied by closing switch S2.

A depolarization of probe SO is achieved via this counter-current pulse or short-circuit pulse. The counter-current pulse or short-circuit pulse is shorter than the pump current pulse. The current intensity of the counter-current pulse can likewise be pregiven. The time integral of the counter-current pulse is so dimensioned that a depolarization of the probe SO as optimal as possible is produced. The counter-current pulse is therefore especially so selected that no polarization results which could affect the pump operation. The pump operation is effected via the pump current pulse. Rather, only a depolarization should take place. The time integral of the pump operation corresponds essentially to the time integral of the probe voltage US which is shown hatched in FIG. 2 and is identified by reference character A. The time integral of the probe voltage is caused by the polarization effects. It has been shown that the duration of the counter-current pulse or short-circuit pulse corresponds approximately to one twentieth to one tenth of the duration of the pump current pulse.

The duration and the current intensity of the counter-current pulse is so selected that the charge QGEG is significantly less than the charge which is generated by the pump current pulses:

$$QGEG \ll QPUMP.$$

The charge QGEG is generated by the counter-current pulse.

The switching state of the switch S3 defines the so-called masking time, that is, the time within which no probe voltage signal is tapped. As shown in FIG. 2, the switch-off duration of the switch S3 is so determined that the probe voltage is not made incorrect, that is, the shift of the probe voltage is not superposed on the actual probe voltage signal. This shift is caused by the pump current pulse as well as by the counter-current pulse or short-circuit pulse.

The arrangement described above and the method are explained with respect to conventional switches (S1, S2, S3). It is understood that the invention is in no way limited to switches of this kind; instead, the switches can be realized in any way. Especially electronic switches in the Form of transistors or other semiconductor components are conceivable for realizing the above-mention device.

It is understood that the foregoing description is that of the preferred embodiments of the invention and that various changes and modifications may be made thereto without departing from the spirit and scope of the invention as defined in the appended claims.

What is claimed is:

1. A method for detecting the oxygen content in a gas to be measured, the method comprising the steps of:

providing at least one concentration cell operating in accordance with the Nernst principle to supply a signal indicative of said oxygen content in said gas with said concentration cell including: a measuring electrode communicating with said gas; a solid electrolyte; and, a reference electrode connected to said measuring electrode through said solid electrolyte;

applying a periodic pump-current pulse between said reference electrode and said measuring electrode; and, directly after the end of each pump-current pulse, applying a counter-current pulse to said concentration cell to reverse the current flow between said reference electrode and said measuring electrode in a pulse-like manner whereby a depolarization of said concentration cell is obtained.

2. The method of claim 1, comprising the further step of applying a counter-current pulse of a pregiven duration and a pregiven current intensity between said reference electrode and said measuring electrode and said current pulse being in a direction opposite to said pump-current pulse.

3. The method of claim 2, comprising the further step of so selecting said duration and said current intensity that the charge generated by said counter-current pulse is markedly less than the charge generated by said pump-current pulse.

4. The method of claim 1, comprising establishing a short circuit of a pregiven duration between said reference electrode and said measuring electrode with said step of applying a counter-current pulse to reverse the current flow.

5. The method of claim 1, wherein said counter-current pulse is shorter than said pump-current pulse.

6. An arrangement for detecting the oxygen content in a gas to be measured, the arrangement comprising:

at least one concentration cell operating on the Nernst principle to supply a signal indicative of said oxygen content in said gas;

said concentration cell including: a measuring electrode communicating with said gas; a solid electrolyte; and, a reference electrode connected to said measuring electrode through said solid electrolyte;

a pump-current source for supplying a periodic pump-current pulse;

first means for coupling in said pump-current pulse between said reference electrode and said measuring electrode;

at least one counter-current source for supplying a counter-current pulse of a pregiven duration and a pregiven current intensity; and, second means for coupling in said counter-current pulse between said reference electrode and said measuring electrode after said pump-current pulse in a direction opposite thereto to obtain a depolarization of said concentration cell.

7. The arrangement of claim 6, wherein said counter-current pulse is shorter than said pump-current pulse.

8. The arrangement of claim 7, wherein the duration of said counter-current pulse is approximately one-twentieth to one-tenth of the duration of said pump-current pulse.

9. The arrangement of claim 6, comprising the further step of adjusting said duration and said current intensity of said counter-current pulse so that the charge generated by said counter-current pulse is significantly less than the charge generated by said pump-current pulse.

10. An arrangement for detecting the oxygen content in a gas to be measured, the arrangement comprising:

at least one concentration cell operating on the Nernst principle to supply a signal indicative of said oxygen content in said gas;

said concentration cell including: a measuring electrode communicating with said gas; a solid electrolyte; and, a reference electrode connected to said measuring electrode through said solid electrolyte;

a pump-current source for supplying a periodic pump-current pulse;

means for coupling in said pump-current pulse between said reference electrode and said measuring electrode; and, switching means for establishing a short circuit or a low ohmic connection between said reference electrode and said measuring electrode over a pregiven time span to obtain a depolarization of said concentration cell.

11. The arrangement of claim 10, wherein said short circuit corresponds to a short-circuit pulse shorter than said pump-current pulse.

12. The arrangement of claim 11, wherein the duration of said short-circuit pulse is approximately one-twentieth to one-tenth of the duration of said pump-current pulse.

* * * * *